United States Patent [19]
Anthony

[11] Patent Number: 5,256,861
[45] Date of Patent: Oct. 26, 1993

[54] METHOD AND APPARATUS FOR ENCAPSULATION AND STERILIZATION OF MEDICAL WASTE SHARPS

[76] Inventor: Frank H. Anthony, 326 Atherton Dr., Metaire, La. 70005

[21] Appl. No.: 682,069

[22] Filed: Apr. 9, 1991

[51] Int. Cl.$^5$ .................................. H05B 1/02
[52] U.S. Cl. ..................... 219/494; 219/390; 219/521; 219/386
[58] Field of Search ............. 219/494, 413, 385, 386, 219/521, 390; 110/346; 423/DIG. 20

[56] References Cited

U.S. PATENT DOCUMENTS

| | | | |
|---|---|---|---|
| 2,027,296 | 1/1936 | Stuart | 206/524.6 |
| 3,136,468 | 6/1964 | Keller | 426/126 |
| 4,018,684 | 4/1977 | Uffer | 210/14 D |
| 4,355,227 | 10/1982 | Berard | 219/386 |
| 4,623,781 | 11/1986 | Thomas | 219/413 |
| 4,897,528 | 1/1990 | Anthony | 219/494 |
| 4,905,916 | 3/1990 | Sorwick et al. | 241/23 |
| 5,003,892 | 4/1991 | Bricken | 219/385 |
| 5,046,669 | 9/1991 | Wallace et al. | 241/23 |

OTHER PUBLICATIONS

Sales Brochure of Koyo Sangyo Co., Ltd.—Koyo Safety Pon—Safety Measured Equipment to Prevent Secondary Infections from Used Syringes, undated.

Primary Examiner—Teresa J. Walberg
Attorney, Agent, or Firm—Nixon & Vanderhye

[57] ABSTRACT

Medical waste, such as hypodermic syringes are placed in a disposable container constructed of single strength corrugated fiberboard with aluminum foil laminated to each surface. The container and used medical sharps are subjected to dry heat treatment at temperatures below the waste material flash point but of sufficient temperature and for a sufficient time to melt the plastic syringe bodies. During the heating process the metal and rubber parts settle within the melted plastic with the aluminum foil layers preventing leakage from the container. Upon cooling the medical sharps are encapsulated in plastic and foil, as well as being sterile such that the container and contents may be discarded with ordinary waste products. The dry heat generator conveniently may be placed in a medical office or the like and is microprocessor controlled to obtain the desired end products. The processor additionally controls an electrical interlock system whereby the heat generator unit may not be opened until an entire heat cycle has been completed, and the waste products have cooled to a safe temperature.

15 Claims, 3 Drawing Sheets

Fig. 1
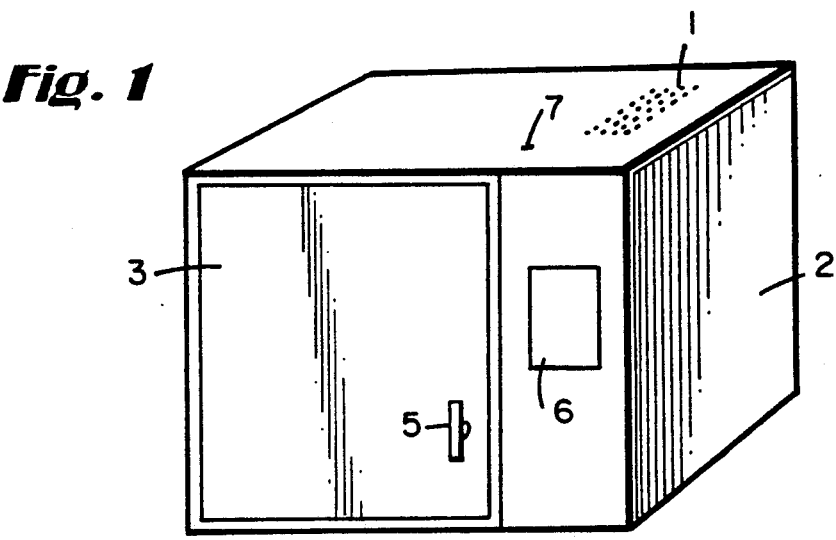
Fig. 2
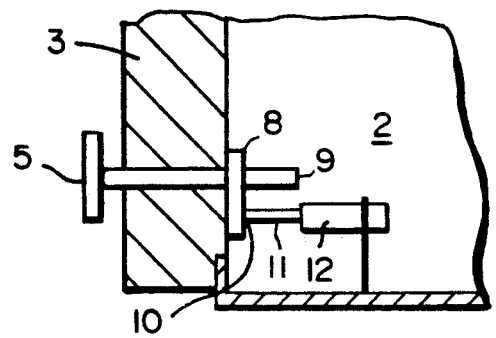
Fig. 2A
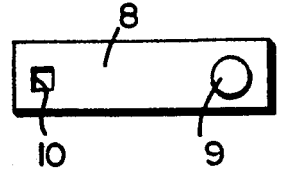
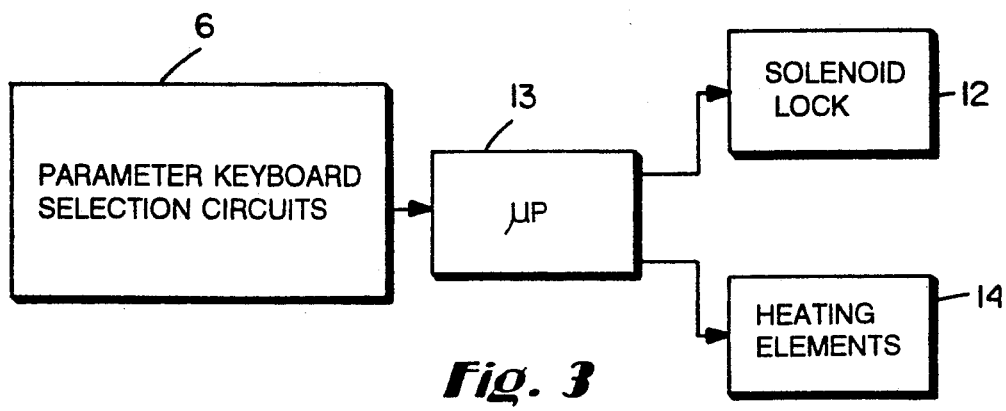
Fig. 3

METHOD AND APPARATUS FOR ENCAPSULATION AND STERILIZATION OF MEDICAL WASTE SHARPS

FIELD OF THE INVENTION

The invention relates to a method and apparatus for treating medical waste sharps to obtain sterilization and encapsulation at relatively low temperatures that are below the flash points of the waste products.

BACKGROUND AND SUMMARY OF THE INVENTION

As is well known, satisfactory disposal methods associated with waste products present formidable problems to industry, governmental agencies and the like. However, the degree of difficulty in dealing with certain waste products such as medical waste is even more difficult in light of the potentially infectious nature of biomedical waste products, such as used syringes.

Recognized methods of treating medical sharps (syringes and the like) include incineration, encapsulation or in some other manner rendering the biomedical waste products safe and unusable. Incineration, however, leads to still further problems, such as air pollution, and still further regulations pertaining to the elimination of metallic compounds from the exhaust fumes. For example, it is known that the red disposal bags presently used for medical waste include significant amounts of cadmium. For incineration, additional measures would be required to prevent the exhaust of such cadmium compounds and other hazardous compounds by way of incinerator exhausts.

Encapsulation in the disposal of medical sharps is also permissible in accordance with some regulations. For example, dentists in some localities may dispose of their used syringes by encapsulating such waste in plaster. Clearly such treatment and handling processes, although authorized, present problems of convenience and practicality and do not eliminate or discourage the problem of illegal dumping.

The principal object of my invention is that of treating medical waste sharps so as to render them harmless the same day of use and at any selected location, such as a doctor's office, thus eliminating any transportation and, therefore, the possibility of dumping untreated potentially infectious biomedical waste.

I have discovered that such objects can be obtained through the use of a dry heat generator that is useful in rendering medical waste, such as syringes and other wastes including plastic elements, harmless by subjecting such items to a heat treatment wherein the temperature is sufficiently high to sterilize the material, as well as to melt the plastic bodies or elements, so that the metal needles and rubber plungers, for example, will sink to the bottom of the thus formed liquid plastic pool. Since the melting temperatures of such materials are substantially below their flash points, the heating function may be controlled both as to time and temperature such that a heating cycle will meet all government regulations pertaining to sterilization and encapsulation but without any burning or incineration of the sharps or other waste products.

It is a further object of this invention to employ a disposable sharps container constructed, for example, of single strength corrugated fiber or cardboard with aluminum foil laminated on each side of the fiber board. Such containers may be used for holding used medical waste until the container is either full or otherwise ready for disposal. When placed in the dry heat generator and subjected to a heating cycle, the corrugated fiber board becomes brittle and easily crumbles. However, the aluminum foil remains intact, thus preventing the melted plastic from leaking from the container. Upon cooling, the top of the container can be pressed down and the entire container discarded as a harmless and relatively small foil wrapped waste product.

It is a still further object of my invention to equip the dry heat generator with a safety lock feature whereby the door of the generator cannot be opened until an entire heat cycle has been completed, and the temperature of the sharps has been reduced to a predetermined safe temperature. The principal object of the safety lock system feature is that of preventing contact with medical wastes that have not been completely treated due to a loss of power, as well as preventing contact with treated sharps prior to cool down to a safe temperature.

A still further object of the invention is to include a high temperature afterburner at an exit port of the dry heat generator, as well as a charcoal filter for treating the fumes including any metallic vapors, in such a manner as to eliminate any metallic or particle contents, as well as removing odors that might be generated in the process.

These and other objects and advantages of the present invention will become more apparent upon reference to the following specification, appended claims and drawings.

BRIEF DESCRIPTION OF THE DRAWINGS

FIG. 1 is a perspective view of an exemplary embodiment of my dry heat generator or autoclave useful in rendering medical waste, such as syringes, safe for disposal;

FIG. 2 is a partial view of the side wall and door of the dry heat generator broken away to illustrate the mechanical and electrically operated lock mechanisms for preventing the opening of the door under potentially hazardous conditions;

FIG. 2A illustrates a side view of an exemplary mechanical latching member associated with the door handle of the dry heat generator;

FIG. 3 illustrates in block diagram form a microprocessor included in the dry heat generator for controlling the electrically operated solenoid door lock and heating elements of the dry heat generator and afterburner heating elements in response to input control information entered by way of pushbuttons or keyboard selection;

DETAILED DESCRIPTION OF THE DRAWINGS

Figure 4:
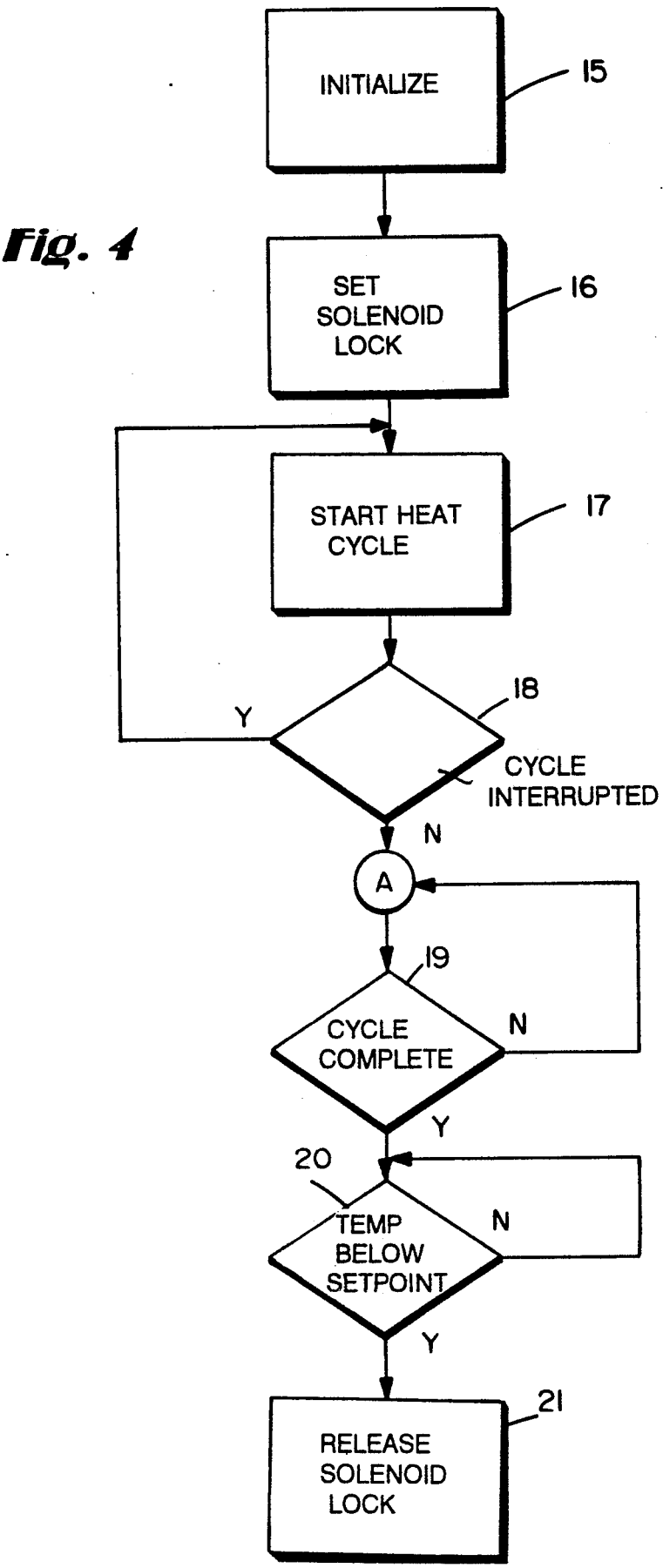
FIG. 4 is a flowchart of the operative steps followed by the microprocessor in the performance of a heating cycle in response to control signals from the input selection circuitry.

Safe disposal of medical waste products have presented formidable problems for some time. Certain of these products, including sharps, such as hypodermic syringes and the like, are particularly troublesome due to the potentially infectious nature of used hypodermic needles in combination with the likelihood of accidental punctures suffered by medical personnel in the handling of such medical sharps. In light of such problems, governmental agencies have enacted laws dictating the requirements and manner of disposing of such waste. One exemplary law pertaining to the treatment of sharps indicates that such waste shall be treated by incineration, encapsulation or other means by which they are rendered unrecognizable as potentially infectious biomedical waste or otherwise rendered unusable.

Incineration or conventional encapsulation methods, however, are not practical or inherently produce additional problems such as air pollution, thus requiring still further legislative action dictating environmental safeguards. Moreover, disposal by conventional encapsulation or incineration methods usually involves repeated handling by various personnel increasing the chance of accidental punctures, as well as generating additional expense which in turn increases the likelihood of unlawful dumping or disposal.

I have discovered that medical waste sharps principally comprising hypodermic syringes having plastic bodies (such as polypropylene) along with the metal needles and rubber stoppers may be safely rendered unrecognizable, encapsulated and sterilized by way of my dry heat autoclave method. Moreover, the method is also applicable to other medical waste having plastic ingredients such as petri dishes, tubing and the like. Such method involves no flame or other heat source which would provide sufficient heat to cause any of the involved materials to reach their flash points. The flash point of the plastic materials involved is approximately 730°, for example; whereas, the melting temperature for plastic syringe material is about 320° F. Accordingly, heating such medical waste at or above the melting point of the plastic material for a sufficient period of time will render the sharps safe at a temperature well below the flash point of the material, as well as rendering such waste sterile and unusable for subsequent use.

Moreover, by placing a number of such sharps in a suitable container and heating the container at a suitable temperature and for a suitable time period, will not only result in the melting of the plastic bodies, but will also allow the stainless steel needles and rubber plungers to sink to the bottom of the now liquid plastic. Upon cooling the plastic will, of course, solidify, thus encapsulating the sharps which may thereafter be safely handled and treated as ordinary waste.

FIG. 1 is a perspective view of an exemplary embodiment of my dry heat generator I which may be sized to conveniently fit on a shelf or desk in a doctor's office, for example. The dry heat generator or autoclave includes a cabinet 2 which may be loaded from the front by way of a hinged door 3, which includes a turnable handle 5 for operating a mechanical latch mechanism. The exemplary dry heat generator additionally includes a row of push buttons or a keyboard selection circuit 6 for selecting cycle parameters, such as temperature and time, as well as other control inputs such as start, set electrical latch, cycle reset and the like.

Additionally included in the interior of the cabinet of the heat generator unit 1 is an afterburner and filter unit connected to the heating chamber of unit 1 by way of an exit port (not shown) and exhausting through the cabinet 2 at vent openings 7. The afterburner unit may be of the nature disclosed in my U.S. Pat. No. 4,897,528 issued on Jan. 30, 1990, which includes a relatively high temperature heating element and condensing path. As described in this patent, the afterburner unit may additionally include a filtering unit such as an activated charcoal filter whereby the exhaust fumes passing through the unit and exiting through vents 7 are acted upon in such a manner as to eliminate any metallic or particulate matter, as well as removing odors that might be generated in the heating process.

As may be seen from a consideration of FIGS. 2 and 2A, handle 5 may be rotated to operate a mechanical latching element, such as 8, by way of shaft 9. Latching element 8 additionally includes an opening 10 for receiving the spring-loaded plunger 11 of solenoid 12. As will be subsequently explained, solenoid 12 and element 11 cooperate with the mechanical latching element 8 so as to form an electrically operated safety lock feature whereby the door 3 of unit 2 cannot be opened until an entire heat cycle has been completed, and the temperature of the sharps in the heating chamber of the unit 2 has been reduced to a predetermined safe temperature. As illustrated, the mechanical and electrical latching mechanisms are included in the side wall of unit 2. Moreover, as will be recognized by the artisan, the mechanical latching mechanism may take various forms including those with keyed or coded locking mechanisms. Provision must be made, however, for the inclusion of an electrical interlock feature of the aforementioned nature.

Additionally included in the insulated walls of the dry heat generator unit 2 is a microprocessor 13, which, as generally illustrated in FIG. 3, receives control inputs from selection circuitry associated with keyboard 6, as well as producing control outputs for operating an electrically operated interlock such as the solenoid 12 and controlling the operation of the heating elements 14 contained within unit 2 as well as in the afterburner.

Microprocessor 13 may be of conventional construction and include nonvolatile memory units such as a random access memory (RAM) for storing input information such as temperature and timing cycle set points, as well as elapsed time data and cycle interrupt flag data. The processor would additionally include a conventional read-only memory (ROM) for storing instructions for implementing the control process illustrated in FIG. 4 in flowchart format.

The control process for implementing the medical waste treatment by my dry heat autoclave method, as illustrated in FIG. 4, begins with an initialization step 15, whereby an appropriate container of sharps or other medical waste is loaded into the chamber of unit 2 with the door mechanically latched and the operator setting an appropriate temperature set point and cycle time by way of keyboard entry means 6. In this regard, although ordinarily maintaining a temperature 320° for a period of two hours and twenty minutes should be sufficient to meet regulations for obtaining sterilized encapsulated sharps, it is contemplated that the minimum set points to be included in the exemplary embodiment would be a temperature set point of about 350° F. with a time period of about three hours in order to assure compliance with governmental regulations. Additional higher set points for both time and temperature may optionally be included for keyboard entry in order to provide for maximum loading of the heat chamber or to provide for materials having higher melting temperatures. All of the available temperature set point selections, however, would be well below the flash points of the waste material to be treated.

Subsequent to the initialization step 15 the operator would proceed to set the electrically operated solenoid lock as at 16, which, for example, may be implemented by way of a start key or button included in keyboard entry means 6 of FIG. 1. Setting of the electrical lock will additionally start the heating cycle, as at 17, wherein electrical energy is supplied to the heating elements of unit 2, as well as the afterburner unit in accordance with the temperature and time set points produced in the nonvolatile RAM memory as in step 15. During the heating cycle, clock pulses supplied by the microprocessor may be used to decrement the selected and stored time period data.

As to temperature control, in addition to storing the selected temperature set point in memory, a thermocouple of the nature taught in my U.S. Pat. No. 4,451,726 which issued on May 29, 1984 may be included in the heat chamber of unit 2 for accurately determining the chamber temperature. Processor 13 repetitively compares the sensed temperature with the temperature set point and reduces or maintains the supply of electrical energy to the chamber heating elements so as to maintain the chamber at the selected desired temperature during the heating cycle.

Additionally, it may be desirable at the beginning of a heating cycle to raise the temperature in stages in a manner similar to that taught in my U.S. Pat. No. 4,367,399 which issued on Jan. 4, 1983. Such a staged increased in temperature would be desirable here since residual fluid may be contained in the hypodermic syringe or other waste products, which should be vaporized and driven off through the afterburner unit prior to melting and possible entrapment of the fluids within the syringe bodies.

After a sufficient time to drive off such residual fluids, which time may be included is the initially set time period, the temperature may be raised to the selected temperature set point which would be sufficient to melt the plastic bodies of the sharps. Presuming no interruption of the heating cycle occurs, such as might occur due to a power outage, the heating cycle proceeds at the selected temperature for the remainder of the time period set by the operator.

However, where a heating cycle has been interrupted, such an event would be detected at step 18 such as by the operation of a solenoid operated switch or other switching device connected to cause a flag bit in memory to be set indicating that an interruption has occurred. Upon reapplication of power, the flag bit would be sensed by processor 13 causing a reinstitution of the heating cycle from the beginning as graphically illustrated by the Y (Yes) response to the interrogation at step 18.

Again presuming no cycle interruption has occurred, the cycle will be maintained until completion, as sensed at step 19. Such cycle completion may be detected by the processor determining that the stored timing cycle data has been decremented to zero. As indicated at step 19 of FIG. 4, the cycle complete step is repetitively performed each time the time period data is reduced until no time is left. Upon detection of a completed heating cycle the microprocessor will de-energize the chamber heating units, as well as instituting step 20 wherein the chamber temperature is continually compared with a pre-stored temperature, such as room temperature, for determining when the heat generator unit 2 may be opened and the contents safely handled. Upon detection of the unit cooling down to the desired safe temperature, the microprocessor will apply electrical energy to the solenoid 12 to thus electrically release the latching mechanism, as at step 21, so that the door 3 may then be opened.

Although in the above noted process the afterburner unit may be de-energized along with the chamber heating units, it is believed that the more desirable procedure would be to de-energize the afterburner element at some later time when the heating chamber of unit 2 is at or near room temperature. The latter procedure would assure continued elimination of metallic contents and odors during the cooling off period, as well as during the heating cycle.

As previously noted, the temperatures in the disclosed dry heat generator are held well below the flash points of the waste materials to be treated, nevertheless, the contemplated temperatures are sufficiently high to melt plastic syringe bodies, for example, and such temperatures would also be sufficiently high to drive off the organics and binders of ordinary cardboard or corrugated box material. Under such circumstances ordinary single strength corrugated box material becomes sufficiently brittle and weak as to allow the liquid plastic contents to escape. Accordingly, I have devised a special purpose container of the nature illustrated in FIGS. 5A and 5B, which may be used by medical personnel for holding used medical waste until the container is either full or otherwise ready for disposal. Thereafter, the disposal container along with its contents may be treated in accordance with the above described process.

Figure 5A:
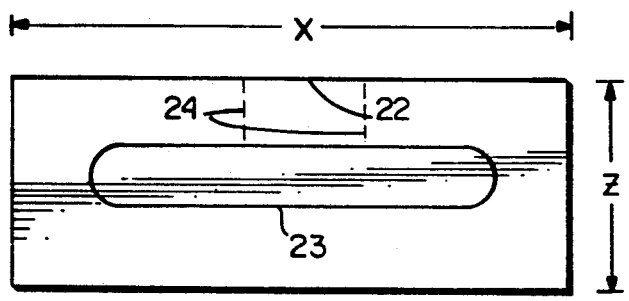
FIGS. 5A and 5B illustrate the top and side views, respectively, of an exemplary container holding medical waste such as sharps for use in the dry heat autoclave or generator of FIG. 1.
Figure 5B:
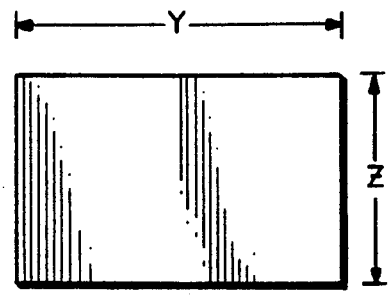

As will be seen from a review of FIGS. 5A and 5B, the disposable medical waste container may be of a rectangular construction as viewed from the top as in FIG. 5A, as well as from the side as shown in FIG. 5B. Although the outside dimensions of the container are generally indicated as x, y and z, exemplary dimensions for x, y and z would be 8 inches, 5 inches and 4 inches, respectively. Additionally, the top of the container as illustrated in FIG. 5 includes a "T" shaped flap attached to the side wall 22 and formed by cutting along solid line 23 and perforating along lines 24 such that the "T" shaped flap may be lifted and the resulting oblong opening used for inserting used medical sharps, for example, into the container. The resulting elongated slot may in the exemplary embodiment be approximately seven inches long and one inch wide for the convenient reception of hypodermic syringes, for example.

Figure 6:
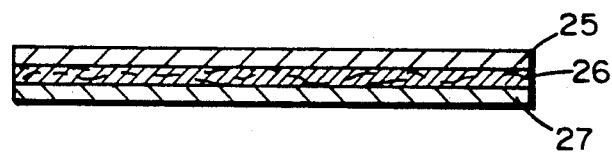
FIG. 6 illustrates the laminated nature of the material to be used in constructing the container of FIGS. 5A and 5B.

As aforementioned, a disposable sharps container constructed of conventional cardboard or corrugated box material, although perhaps adequately serving as a convenient receptacle for used medical sharps prior to treatment, would not adequately serve to prevent leakage of the liquid plastic during heat treatment. I have found, however, that fabricating the container of a laminated material, as generally illustrated in FIG. 6, for example, will perform well both before and during the heat treatment. As illustrated, the material includes a layer 26 of single strength corrugated box material with aluminum foil layers 25 and 27 attached to each side of the layer 26. A container thus formed will provide a relatively sturdy container for receiving used medical sharps and will additionally provide a highly leak resistant container for use during the heating process. That is to say, although during the process layer 26 will become quite brittle due to organics and binders decomposing at the contemplated heating cycle temperatures, the aluminum foil layers remain in tact, thus preventing the melted plastic bodies from leaking from the container. Moreover, upon cooling, the top of the remaining container can be pressed down and the entire container thereafter discarded as a harmless and relatively small foil wrapped waste product.

As will be appreciated by those skilled in the art, a single foil layer on only the outer container surface may be sufficient to prevent the aforementioned leakage under some circumstances. The presently preferred embodiment, however, includes at least one such foil layer on both the interior and exterior surfaces of the container. Moreover, for additional puncture protection, further layers may be added to that which is illustrated in FIG. 6.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A heat generator apparatus for treating potentially infectious waste products which include plastic elements, said apparatus comprising:
    a chamber including a front loading door and heating elements for heating said chamber to a selectable temperature;
    input means for setting said selectable temperature and for setting a selectable time period for maintaining the selected temperature;
    said selectable temperatures and uninterrupted time periods, in combination being at least sufficient to sterilize said waste products and melt said plastic bodies to form a plastic pool, said selectable temperatures additionally being below the flash points of said waste products;
    control means responsive to said input means for controlling said heating elements to raise and maintain the chamber temperature to said selected temperature for the selected time period;
    said control means including means for detecting an interruption and the restoration of power to said apparatus; and
    means responsive to said detecting means for again raising and maintaining said chamber temperature to said selected temperature for the full selected time period upon the restoration of power.

2. An apparatus as in claim 1 further including:
    means connected to said chamber for treating the fumes from the heated waste products to substantially remove odors as well as metallic and particle contents from said fumes.

3. An apparatus as in claim 1 further including:
    means for accessing said chamber via said front loading door, and
    electrically operated means responsive to said input means and said control means for preventing the use of said accessing means until said chamber temperature has been raised and maintained at said selected temperature for said full selected time period.

4. An apparatus as in claim 3 wherein said means for preventing is further responsive to said control means for preventing use of said accessing means until the temperature of said waste products has been reduced to about room temperature.

5. An apparatus as in claim 1 wherein said control means includes means for initially raising said chamber to a temperature below said selected temperature so as to vaporize residual fluids contained in said waste products and subsequently raising the chamber temperature to said selected temperature.

6. An apparatus as in claim 1 wherein said waste products are enclosed in a container in said chamber, and
    said container is constructed of a material which when heated will prevent said liquid pool from leaking from the container.

7. An electrical interlock apparatus for use in a microprocessor controlled medical waste dry heat generator unit, said unit including a cabinet containing a chamber for heating said waste products at a selected temperature for a selected time period and further including a front loading door with a mechanical door latch, said apparatus including:
    means for detecting a power interruption and restoration to said unit during a said selected time period;
    electrically operated means associated with said mechanical door latch for selectively preventing said latch from being operated to open said door;
    means in said microprocessor responsive to said detecting means detecting a said power interruption and restoration for controlling said means for selectively preventing so as to prevent the opening of said door until the chamber has been heated to said selected temperature for the full selected time period without a power interruption.

8. An apparatus as in claim 7 further comprising:
    means for sensing the temperature of said chamber; and
    further means in said microprocessor responsive to said temperature sensing means for causing said means for selectively preventing to prevent the opening of said door until the temperature of said chamber has been reduced to about room temperature.

9. An apparatus as in claim 8 wherein said means for selective preventing comprises a solenoid operated engagement mechanism.

10. An apparatus as in claim 7 further including means in said microprocessor for initially raising said chamber to a temperature below said selected temperature so as to vaporize residual fluids contained in said waste products and then subsequently raising the chamber temperature to said selected temperature.

11. A method of heat treating potentially infectious waste products which include plastic elements, said method comprising the steps of:
    placing said waste products in a container;
    heating said container at a first temperature below the melting point of said plastic elements for a first time period sufficient to vaporize residual fluids contained in said waste products;
    heating said waste products for a second time period at a second temperature above the melting point of said plastic elements but below the flash points of said waste products;
    said first and second temperatures and uninterrupted time periods, in combination, being sufficient to sterilize said waste products and melt said plastic elements;

detecting an interruption and restoration of power supplying said heating, and upon detecting the restoration of power again heating said container at said first and second temperatures for the full first and second time periods, respectively.

12. A method as in claim 11 wherein said container and its contents are placed in a dry heat generator prior to heating.

13. A method as in claim 12 further including the step of:

providing said dry heat generator with means for preventing access to said container and its contents until they have been heated at said first and second temperatures for said full first and second periods of time.

14. A method as in claim 11 further comprising the step of:

treating the fumes from the heated container and its contents to substantially remove odors as well as metallic and particle contents.

15. A method as in claim 11 further comprising the step of:

preventing access to said container and its contents after heating until they have cooled to substantially room temperature.

* * * * *